US010757302B2

(12) United States Patent
Usuda et al.

(10) Patent No.: US 10,757,302 B2
(45) Date of Patent: Aug. 25, 2020

(54) SMALL, SOLID-STATE IMAGING MODULE AND HARNESS UNIT

(71) Applicant: FUJIKURA LTD., Tokyo (JP)

(72) Inventors: Hideaki Usuda, Tokyo (JP); Takeshi Ishizuka, Sakura (JP)

(73) Assignee: Fujikura Ltd., Tokyo (JP)

( * ) Notice: Subject to any disclaimer, the term of this patent is extended or adjusted under 35 U.S.C. 154(b) by 0 days.

(21) Appl. No.: 16/107,663

(22) Filed: Aug. 21, 2018

(65) Prior Publication Data

US 2019/0068848 A1    Feb. 28, 2019

(30) Foreign Application Priority Data

Aug. 31, 2017 (JP) ................. 2017-167994

(51) Int. Cl.
*H04N 5/225* (2006.01)
*H04N 5/335* (2011.01)
(Continued)

(52) U.S. Cl.
CPC .......... *H04N 5/2253* (2013.01); *A61B 1/051* (2013.01); *H01L 27/14603* (2013.01); *H04N 5/335* (2013.01); *H04N 2005/2255* (2013.01)

(58) Field of Classification Search
CPC ........... H04N 5/2253; H04N 5/335; H04N 2005/2255; H01L 27/14603; A61B 1/051
See application file for complete search history.

(56) References Cited

U.S. PATENT DOCUMENTS 4,831,456 A * 5/1989 Takamura ............ H04N 5/2253
348/294
5,879,285 A    3/1999 Ishii
(Continued)

FOREIGN PATENT DOCUMENTS

EP    2790218 A1    10/2014
JP    H0990237 A    4/1997
(Continued)

OTHER PUBLICATIONS

Extended European Search Report issued in corresponding European Patent Application 18188621.9 dated Mar. 8, 2019 (8 pages).

*Primary Examiner* — Gevell V Selby
(74) *Attorney, Agent, or Firm* — Osha Liang LLP

(57) ABSTRACT

The imaging module includes: an image-sensing device, circuit substrate, fixing member, signal cable, and electroconductive member. The image-sensing device includes: a connection electrode. The circuit substrate includes: a substrate main body, electrode terminal, cable terminal, and connection wiring. The substrate main body has two surfaces and is an insulating member. The electrode terminal is on the first surface and is electrically connected to the connection electrode. The cable terminal is on the second surface. Inside the substrate main body, the connection wiring electrically connects the electrode terminal to the cable terminal. The fixing member has a through hole and a substrate connection face opposite the second surface. The signal cable is inserted into the through hole and is fixed by the fixing member. The electroconductive member connects the second surface to the substrate connection face and electrically connects the conductor end face to the cable terminal.

11 Claims, 6 Drawing Sheets

(51) Int. Cl.
*H01L 27/146* (2006.01)
*A61B 1/05* (2006.01)

(56) References Cited

U.S. PATENT DOCUMENTS

| | | | | |
|---|---|---|---|---|
| 2007/0167814 A1* | 7/2007 | Wakabayashi | ........... | A61B 8/12 600/459 |
| 2012/0104230 A1* | 5/2012 | Eismann | .............. | H04N 5/2253 250/208.1 |
| 2012/0271108 A1* | 10/2012 | Hoshino | ............ | A61B 1/00009 600/139 |

FOREIGN PATENT DOCUMENTS

| | | |
|---|---|---|
| JP | H1028672 A | 2/1998 |
| JP | 2006-109097 A | 4/2006 |
| JP | 2013118337 A | 6/2013 |
| JP | 2015-062555 A | 4/2015 |
| JP | 2016-131709 A | 7/2016 |
| WO | 2011007674 A1 | 1/2011 |

* cited by examiner

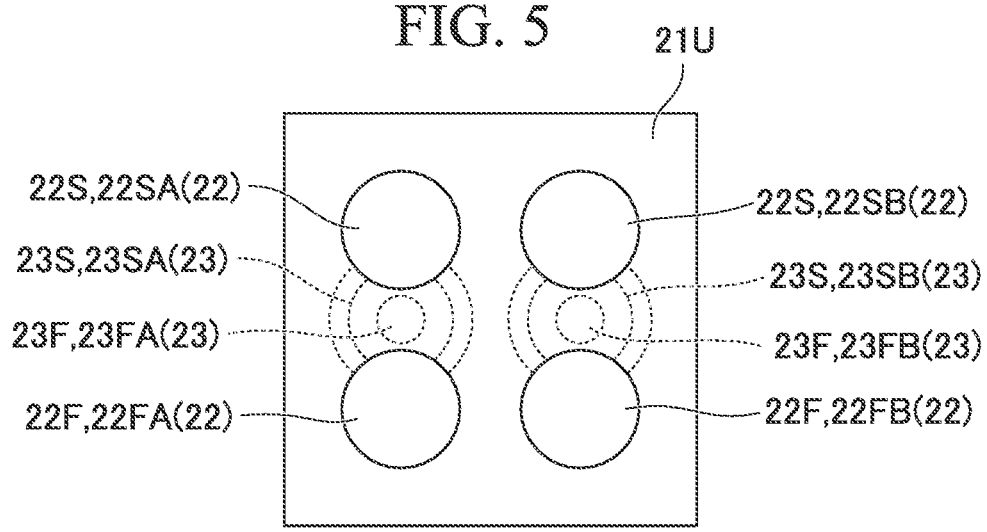
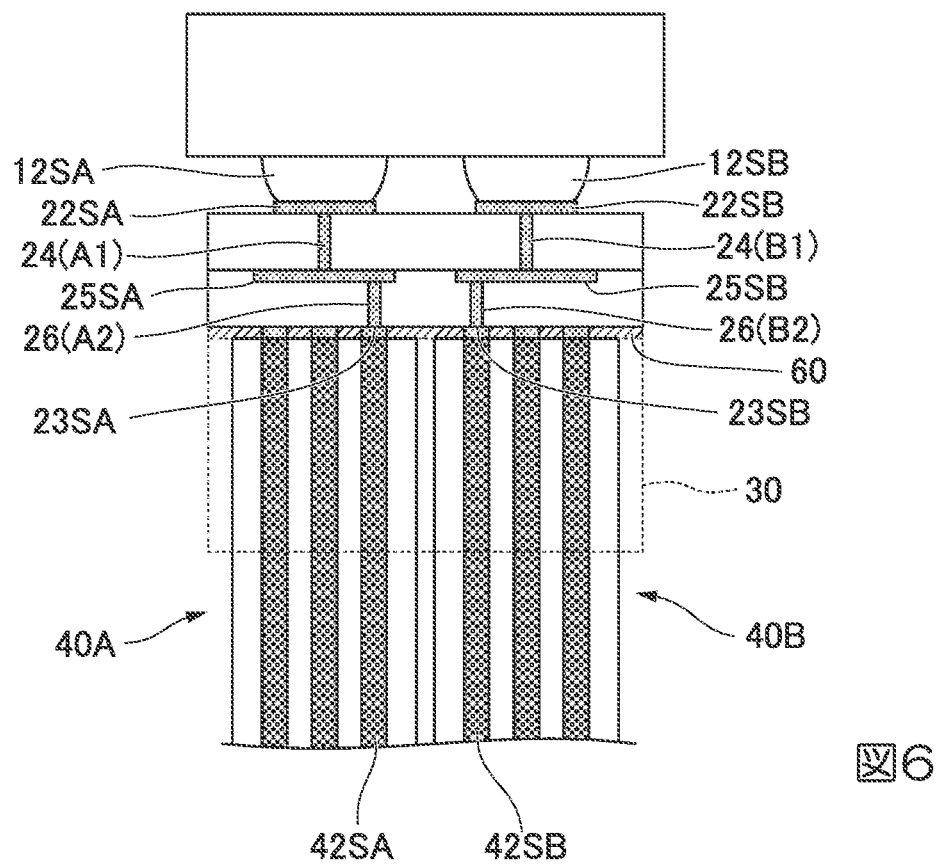

SMALL, SOLID-STATE IMAGING MODULE AND HARNESS UNIT

CROSS REFERENCE TO RELATED APPLICATIONS

This application claims priority from Japanese Patent Application No. 2017-167994 filed on Aug. 31, 2017, the contents of which are incorporated herein by reference in their entirety.

TECHNICAL FIELD

The present invention relates to an imaging module and a harness unit.

BACKGROUND

An imaging module having a configuration in which a solid-state image sensing device (hereinbelow, may be simply referred to as an image-sensing device) is electrically connected to an end of an electrical cable with a wiring substrate interposed therebetween is often employed in electronic endoscopes (for example, Japanese Unexamined Patent Application, First Publication No. 2006-109097).

In this kind of imaging module, a plurality of ends of the electrical cable are electrically connected to wiring of the wiring substrate, and each electrical cable is electrically connected to the image-sensing device via the wiring of the wiring substrate.

In the aforementioned imaging module, an insulating coating of a signal cable is removed, a conductor is exposed, and the conductor is connected to a circuit substrate by soldering. In this connecting method, in order to connect the circuit substrate and the conductor, it is necessary to expose the conductor by a length (a length of the signal cable in the extending direction) required for connecting the signal cable and the circuit substrate by soldering or the like. Consequently, a length of the imaging module becomes longer by the length of the exposed portion of the conductor, making it difficult to reduce the imaging module in size.

SUMMARY

One or more embodiments of the invention provide a small imaging module that can shorten a length required for connecting a signal cable to a circuit substrate, and a harness unit that achieves the small imaging module.

An imaging module according to one or more embodiments includes: an image-sensing device including a connection electrode; a circuit substrate including a substrate main body that has a first surface and a second surface opposite to the first surface and serves as an insulating member, an electrode terminal that is formed on the first surface and is electrically connected to the connection electrode, a cable terminal formed on the second surface, and a connection wiring that is formed inside the substrate main body and electrically connects the electrode terminal to the cable terminal; a fixing member having a substrate connection face disposed so as to face the second surface and a through hole; a signal cable that includes a conductor having a conductor end face, is inserted into the through hole, and is fixed by the fixing member; and an electroconductive member that is disposed between the second surface and the substrate connection face, connects the second surface to the substrate connection face, and electrically connects the conductor end face to the cable terminal at between the second surface and the substrate connection face.

In the imaging module according to one or more embodiments, the conductor end face and the substrate connection face may be located on the same plane.

In the imaging module according to one or more embodiments, the conductor may have a conductor protrusion that protrudes from the substrate connection face, and the conductor end face may be formed on the conductor protrusion.

In the imaging module according to one or more embodiments, the fixing member may include an adhesive provided between an inner wall of the through hole and an outer surface of the signal cable.

In the imaging module according to one or more embodiments, the fixing member may include an adhesion portion at which an inner wall of the through hole attached firmly to an outer surface of the signal cable.

In the imaging module according to one or more embodiments, the conductor of the signal cable may include an internal conductor having an internal conductor end face and an external conductor having an external conductor end face, the cable terminal may have a first cable terminal and a second cable terminal different from the first cable terminal, the internal conductor end face may be electrically connected to the first cable terminal with the electroconductive member interposed therebetween at between the second surface and the substrate connection face, and the external conductor end face may be electrically connected to the second cable terminal with the electroconductive member interposed therebetween the second surface and the substrate connection face.

In the imaging module according to one or more embodiments, the electrode terminal may have a first electrode terminal and a second electrode terminal different from the first electrode terminal, the connection wiring may have a first connection wiring and a second connection wiring different from the first connection wiring, the first cable terminal may be electrically connected to the first electrode terminal with the first connection wiring interposed therebetween, and the second cable terminal may be electrically connected to the second electrode terminal with the second connection wiring interposed therebetween.

A harness unit according to one or more embodiments includes: a fixing member having a connection face that faces a connection object, and a through hole; and a signal cable that includes a conductor having a conductor end face, is inserted into the through hole, and is fixed by the fixing member, wherein the conductor end face is exposed at the connection face.

In the harness unit according to one or more embodiments, the conductor end face and the connection face may be located on the same plane.

In the harness unit according to one or more embodiments, the conductor may have a conductor protrusion that protrudes from the connection face, and the conductor end face may be formed on the conductor protrusion.

In the harness unit according to one or more embodiments, the conductor of the signal cable may include: an internal conductor having an internal conductor end face; and an external conductor having an external conductor end face.

In the harness unit according to one or more embodiments, the fixing member may include an adhesive provided between an inner wall of the through hole and an outer surface of the signal cable.

In the harness unit according to one or more embodiments, the fixing member may include an adhesion portion at which an inner wall of the through hole attached firmly to an outer surface of the signal cable.

Effects of the Invention

According to the above-mentioned aspect of one or more embodiments, between the second surface of the circuit substrate (connection object) and the substrate connection face (connection face) of the fixing member, it is possible to connect the conductor end face and the cable terminal. Accordingly, since a length required for connecting a signal cable to a circuit substrate can be shorter than in a conventional case, the length of the imaging module can be shorter than in a conventional case. As a result, it is possible to provide a small imaging module. Moreover, it is possible to provide a harness unit that achieves the small imaging module.

BRIEF DESCRIPTION OF THE DRAWINGS

FIG. 5 is an explanatory plan view showing a positional relationship between an electrode terminal and a cable terminal on the circuit substrate constituting the imaging module according to one or more embodiments of the invention.

FIG. 6 is an explanatory cross-sectional view showing an electrical connection structure of the solid-state image sensing device, the circuit substrate, and the fixing member, which constitute the imaging module according to one or more embodiments of the invention.

DETAILED DESCRIPTION

Figure 1:
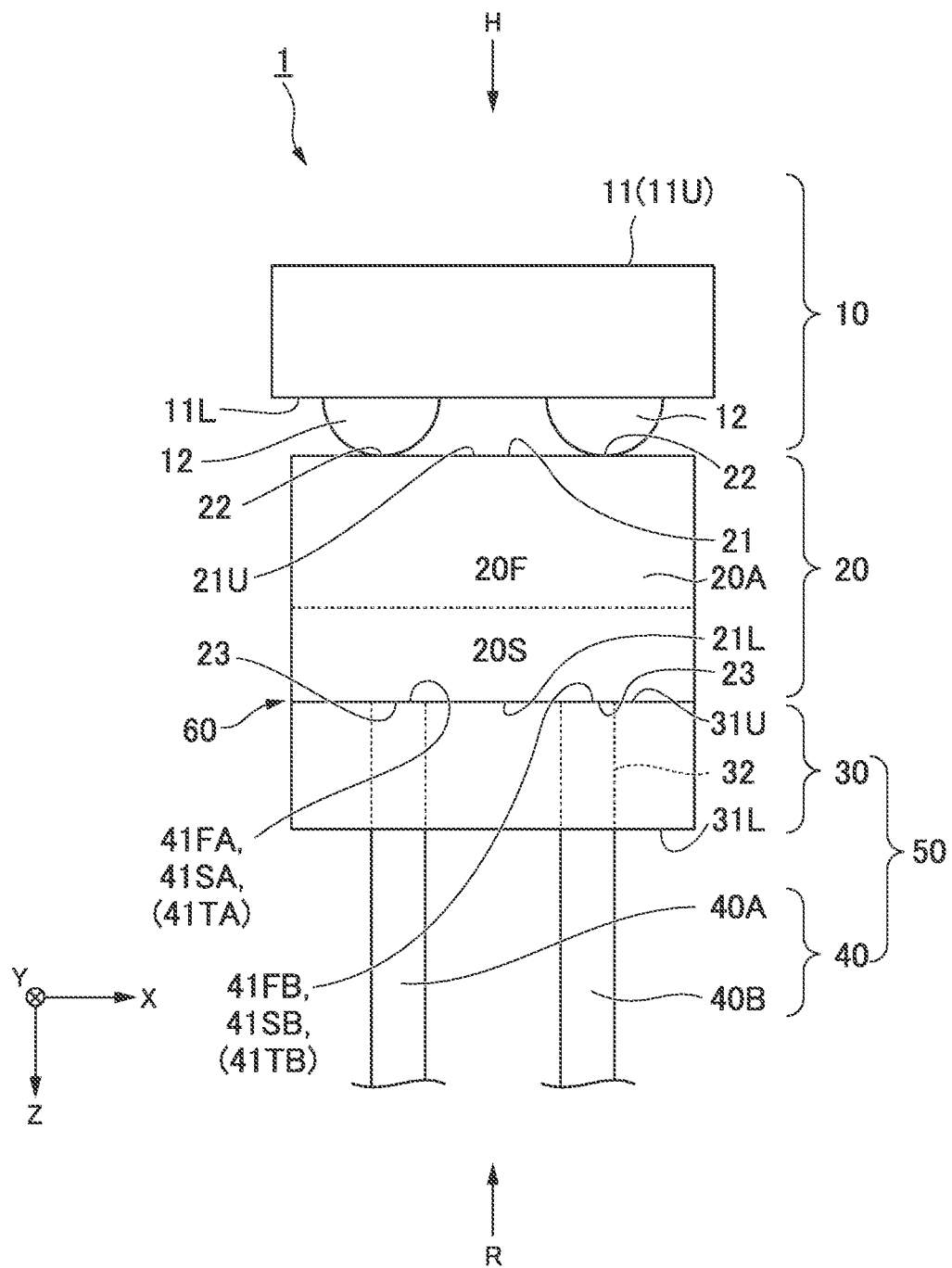
FIG. 1 is a side view showing a schematic configuration of an imaging module according to one or more embodiments of the invention.

Hereinafter, embodiments of the invention will be described with reference to drawings.

In the drawings showing one or more embodiments of the invention, in order for the respective components to be of understandable size in the drawings, the dimensions and the proportions of the components are modified as needed compared with the real components.

In the following description, the XYZ coordinate system is used. The XY-direction is a direction parallel to a light-receiving face of a solid-state image sensing device 10, and the Z-direction is the same direction as the direction H vertical to the light-receiving face of the solid-state image sensing device 10. In the following description, "plan view" means the plane when viewed in the direction H.

FIG. 1 is a side view showing a schematic configuration of the imaging module according to one or more embodiments of the invention 1. The imaging module 1 includes a solid-state image sensing device 10 (image-sensing device), a circuit substrate 20, a fixing member 30, a transmission harness 40 (signal cable), and an electroconductive member 60. The fixing member 30 and the transmission harness 40 constitute a harness unit 50 according to one or more embodiments of the invention. The length of the imaging module in the Z-direction is, for example, less than or equal to 5 mm. In addition, the chip size of the solid-state image sensing device 10 in plan view is less than or equal to 1 mm×1 mm. In a plan view, as a result of reducing the circuit substrate 20, the fixing member 30, and the transmission harness 40 in size so as to be smaller than the chip size of the solid-state image sensing device 10, it is possible to achieve an imaging module having a small-diameter.

(Solid-State Image Sensing Device 10)

Figure 2A:
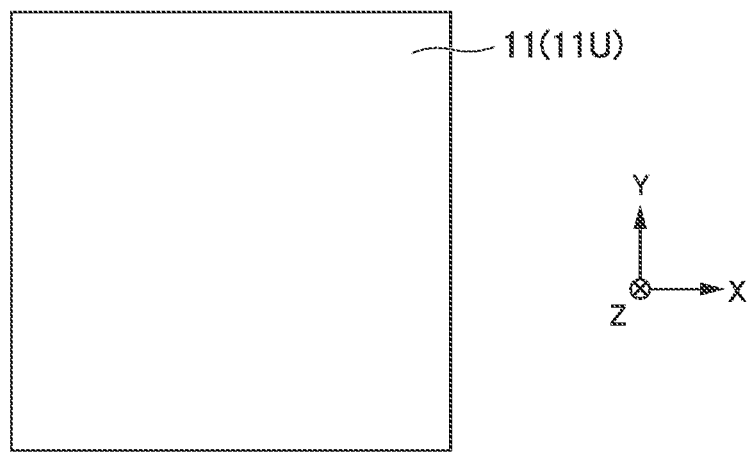
FIG. 2A is a top view showing a schematic configuration of a solid-state image sensing device constituting the imaging module according to one or more embodiments of the invention.
Figure 2B:
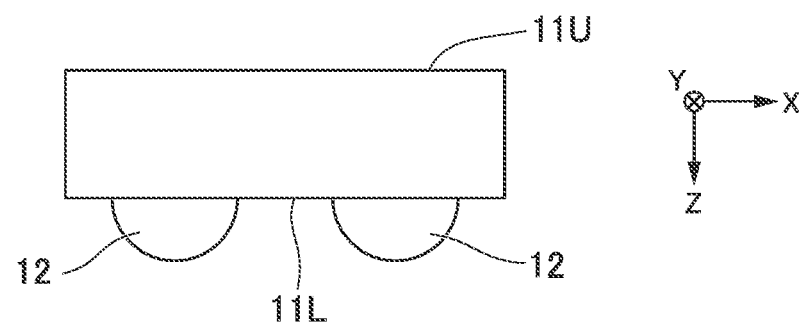
FIG. 2B is a side view showing a schematic configuration of the solid-state image sensing device constituting the imaging module according to one or more embodiments of the invention.
Figure 2C:
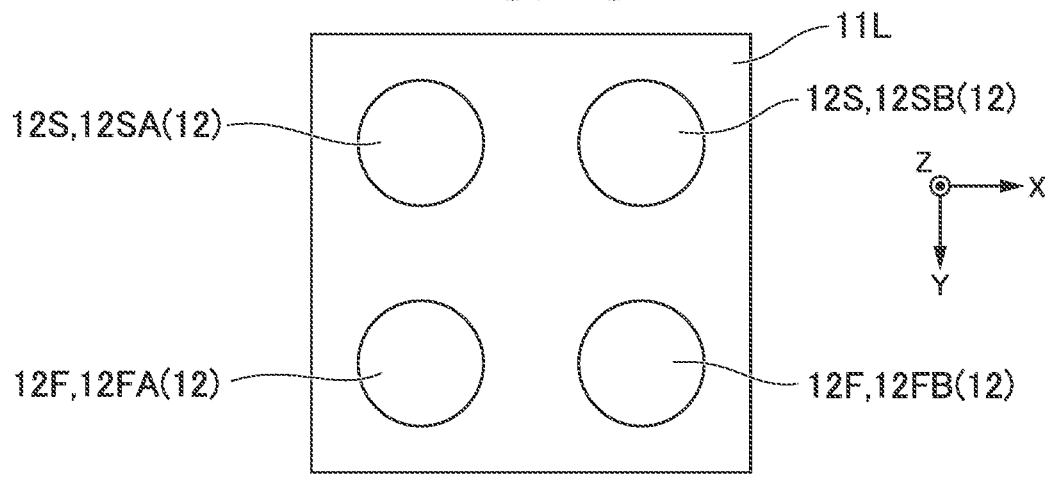
FIG. 2C is a bottom view showing a schematic configuration of the solid-state image sensing device constituting the imaging module according to one or more embodiments of the invention.

FIGS. 2A to 2C are views each showing a schematic configuration of the solid-state image sensing device 10 constituting the imaging module 1.

FIG. 2A is a top view showing the solid-state image sensing device 10 when viewed in the direction H. FIG. 2B is a side view showing the solid-state image sensing device 10. FIG. 2C is a bottom view showing the solid-state image sensing device 10 when viewed in the direction R opposite to the direction H.

The solid-state image sensing device 10 includes: a light-receiving face 11 located on an upper face 11U of the solid-state image sensing device 10; and connection electrodes 12 provided on a lower face 11L of the solid-state image sensing device 10. A lens unit such as an object lens may be mounted on the light-receiving face 11. The solid-state image sensing device 10 has BGA (Ball Grid Array) structure which is generally known. As the solid-state image sensing device 10, for example, a CMOS (complementary metal oxide semiconductor) is used.

As shown in FIG. 2C, four connection electrodes 12, that is, connection electrodes 12FA (12F), 12SA (12S), 12FB (12F), and 12SB (12S) are provided on the lower face 11L.

The connection electrode 12FA is electrically connected to an internal conductor 42FA of a first harness 40A. The connection electrode 12SA is electrically connected to an external conductor 42SA of the first harness 40A. The connection electrode 12FB is electrically connected to an internal conductor 42FB of a second harness 40B. The connection electrode 12SB is electrically connected to an external conductor 42SB of the second harness 40B. Specific wiring structure of the imaging module 1 will be described later.

(Circuit Substrate 20)

Figure 3A:
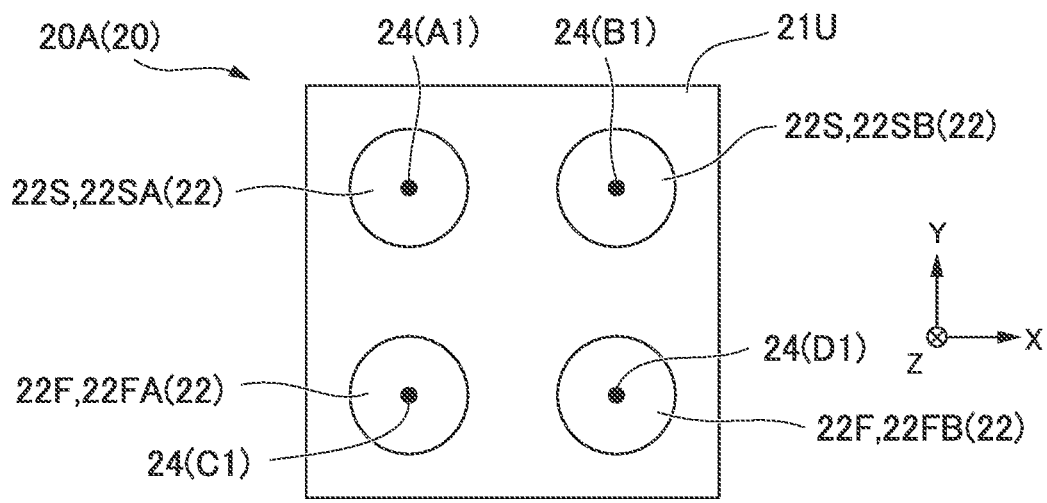
FIG. 3A is a top view showing a schematic configuration of a circuit substrate constituting the imaging module according to one or more embodiments of the invention.
Figure 3B:
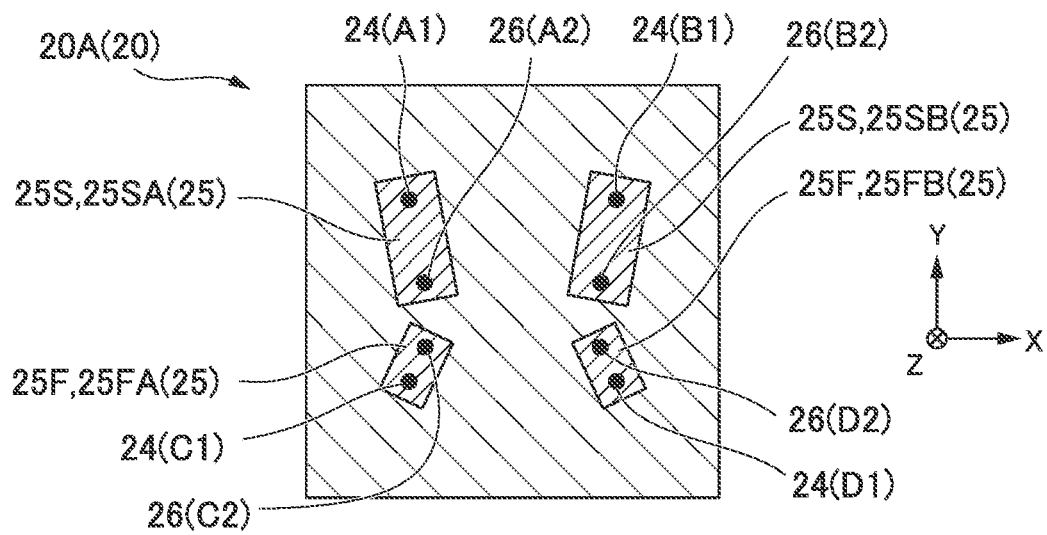
FIG. 3B is a side view showing a schematic configuration of the circuit substrate constituting the imaging module according to one or more embodiments of the invention.
Figure 3C:
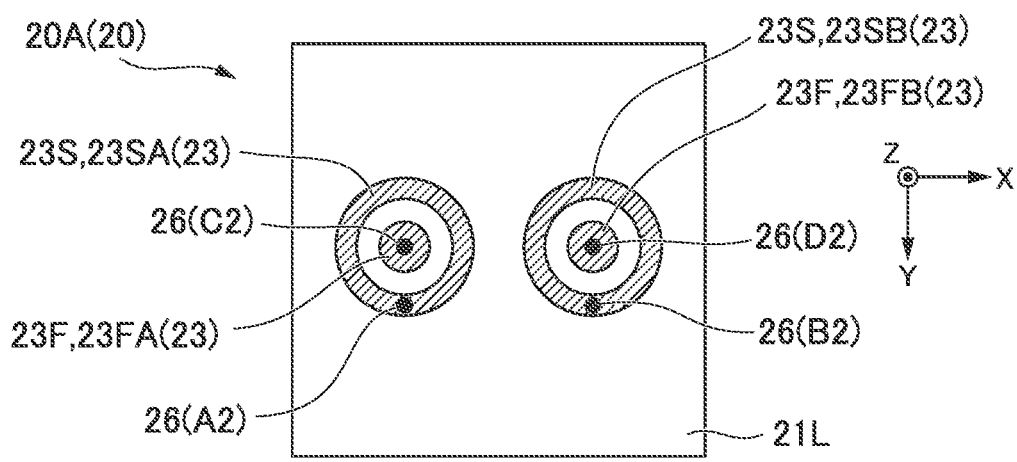
FIG. 3C is a bottom view showing a schematic configuration of the circuit substrate constituting the imaging module according to one or more embodiments of the invention.

FIGS. 3A to 3C are views each showing a schematic configuration of the circuit substrate 20 constituting the imaging module 1. FIG. 3A is a top view showing the circuit substrate 20 shown in FIG. 1. FIG. 3B is a cross-sectional view showing a portion between a first region 20F and a second region 20S of the circuit substrate 20 shown in FIG. 1. FIG. 3C is a bottom view showing the circuit substrate 20 shown in FIG. 1. It is not necessarily the case that a boundary is formed between the first region 20F and the second region 20S. In the case where the circuit substrate 20 is molded by an electrical conductor and an insulator and thereby forms an integrated body, a boundary is not formed between the first region 20F and the second region 20S.

The circuit substrate 20 is, for example, a printed board having wirings formed thereinside. Note that, the structure of the circuit substrate 20 is not limited to the printed board, and a ceramic substrate may be adopted. Additionally, a wafer on which the solid-state image sensing device 10 is formed may be used as the circuit substrate 20. In this case, the wafer is direct connected to the transmission harness 40 (harness unit 50).

The circuit substrate 20 includes a substrate main body 20A, electrode terminals 22, cable terminals 23, and connection wirings 24, 25, and 26. The substrate main body 20A is made of an insulating member such as resist and has a substrate upper face 21U (first surface) and a substrate lower face 21L (second surface opposite to the first surface).

The electrode terminals 22 are formed so as to be exposed from the substrate upper face 21U and are electrically connected to the connection electrodes 12. The electrode terminals 22 function as pads formed on the substrate upper face 21U.

The cable terminals 23 are formed so as to be exposed from the substrate lower face 21L and are electrically connected to a conductor end face of the transmission harness 40 (which will be described later). The cable terminals 23 function as pads formed on the substrate lower face 21L.

The connection wirings 24, 25, and 26 are formed inside the substrate main body 20A and electrically connect the electrode terminals 22 and the cable terminals 23. Resist forming the substrate main body 20A provided around each of the connection wirings 24, 25, and 26, the connection wirings 24, 25, and 26 are each electrically independent.

As shown in FIG. 3A, four electrode terminals 22FA, 22SA, 22FB, and 22SB are provided on the substrate upper face 21U. Four the connection wirings 24(C1), 24(A1), 24(D1), and 24(B1) are provided inside the substrate main body 20A so as to correspond to the electrode terminals 22FA, 22SA, 22FB, and 22SB, respectively.

The electrode terminal 22FA (first electrode terminal) is located on an upper face of the connection wiring 24(C1) and is electrically connected to the connection wiring 24(C1). The electrode terminal 22FA is electrically connected to the connection electrode 12FA.

The electrode terminal 22SA (second electrode terminal) is located on an upper face of the connection wiring 24(A1) and is electrically connected to the connection wiring 24(A1). The electrode terminal 22SA is electrically connected to the connection electrode 12SA.

The electrode terminal 22FB (first electrode terminal) is located on an upper face of the connection wiring 24(D1) and is electrically connected to the connection wiring 24(D1). The electrode terminal 22FB is electrically connected to the connection electrode 12FB.

The electrode terminal 22SB (second electrode terminal) is located on an upper face of the connection wiring 24(B1) and is electrically connected to the connection wiring 24(B1). The electrode terminal 22SB is electrically connected to the connection electrode 12SB.

As shown in FIG. 3B, four connection wirings 25, that is, connection wirings 25FA(25F), 25SA(25S), 25FB(25F), 25SB(25S) are provided inside the substrate main body 20A.

The connection wiring 25FA electrically connects the connection wiring 24(C1) to the connection wiring 26(C2). The connection wiring 25SA electrically connects the connection wiring 24(A1) to the connection wiring 26(A2). The connection wiring 25FB electrically connects the connection wiring 24(D1) to the connection wiring 26(D2). The connection wiring 25SB electrically connects the connection wiring 24(B1) to the connection wiring 26(B2).

As shown in FIG. 3C, four cable terminals 23FA, 23SA, 23FB, and 23SB are provided on the substrate lower face 21L. Four connection wirings 26(C2), 26(A2), 26(D2), and 26(B2) are provided inside the substrate main body 20A so as to correspond to the cable terminals 23FA, 23SA, 23FB, and 23SB, respectively.

The connection wiring 26(A2) is formed so as to surround the connection wiring 26(C2), that is, the connection wiring 26(C2) and the connection wiring 26(A2) are arranged in a concentric form.

Similarly, the connection wiring 26(B2) is formed so as to surround the connection wiring 26(D2), that is, the connection wiring 26(D2) and the connection wiring 26(B2) are arranged in a concentric form.

The cable terminal 23FA (first cable terminal) is located on a lower face of the connection wiring 26(C2) and is electrically connected to the connection wiring 26(C2). The cable terminal 23FA is electrically connected to an internal conductor end face 41FA through the electroconductive member 60 (which will be described later) and the cable terminal 23FA.

The cable terminal 23SA (second cable terminal) is located on a lower face of the connection wiring 26(A2) and is electrically connected to the connection wiring 26(A2). The cable terminal 23SA is electrically connected to an external conductor end face 41SA through the electroconductive member 60 and the cable terminal 23SA.

The cable terminal 23FB (first cable terminal) is located on a lower face of the connection wiring 26(D2) and is electrically connected to the connection wiring 26(D2). The cable terminal 23FB is electrically connected to an internal conductor end face 41FB through the electroconductive member 60 and the cable terminal 23FB.

The cable terminal 23SB (second cable terminal) is located on a lower face of the connection wiring 26(B2) and is electrically connected to the connection wiring 26(B2). The cable terminal 23SB is electrically connected to external conductor end face 41SB through the electroconductive member 60 and the cable terminal 23SB.

The circuit substrate 20 having the aforementioned structure is a multi-layered wiring substrate in which the electrode terminal 22, the connection wiring 25, and the cable terminal 23 are layered via insulating members. Through holes are formed in this multi-layered wiring substrate, and the connection wirings 24 and 26 are implanted into the through holes (implanted wiring). The connection wirings 24 and 26 extend in the Z-direction, and the connection wiring 25 extends in the XY-direction.

Wiring patterns of the electrode terminal 22, the connection wirings 24, 25, and 26, and the cable terminal 23 can be modified depending on arrangement the connection electrode 12 of the solid-state image sensing device 10 or arrangement of the transmission harness 40 fixed by the fixing member 30.

(Fixing Member 30)

FIGS. 4A to 4D are views each showing a schematic configuration of the fixing member 30 constituting the imaging module 1.

Figure 4A:
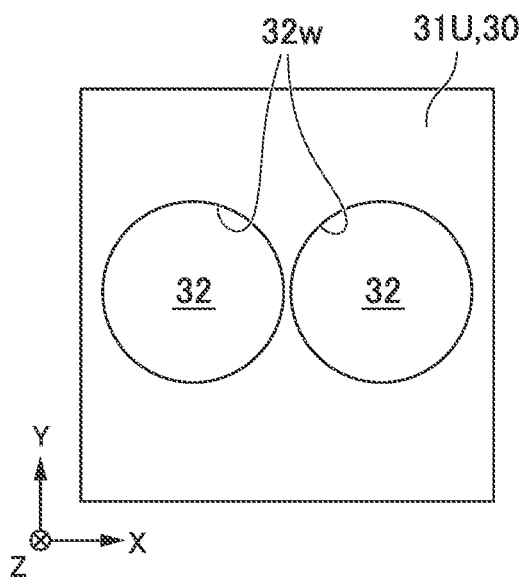
FIG. 4A is a top view showing a schematic configuration of a fixing member constituting the imaging module according to one or more embodiments of the invention.
Figure 4D:
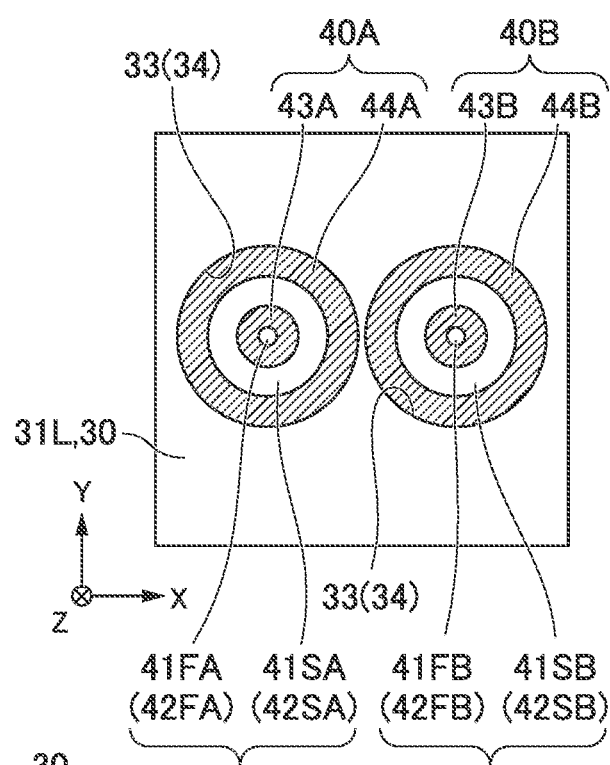
FIG. 4D is a top view showing a schematic configuration of the fixing member constituting the imaging module according to one or more embodiments of the invention and is a view showing a state where a transmission harness is inserted into and fixed to a through hole of the fixing member.
Figure 4B:
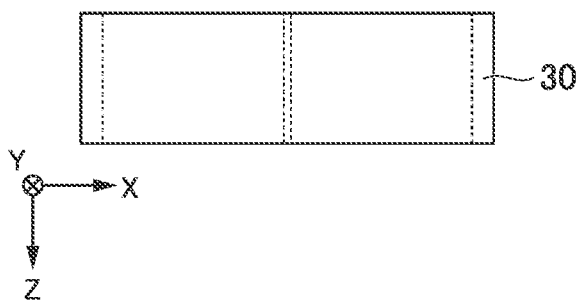
FIG. 4B is a side view showing a schematic configuration of the fixing member constituting the imaging module according to one or more embodiments of the invention.
Figure 4C:
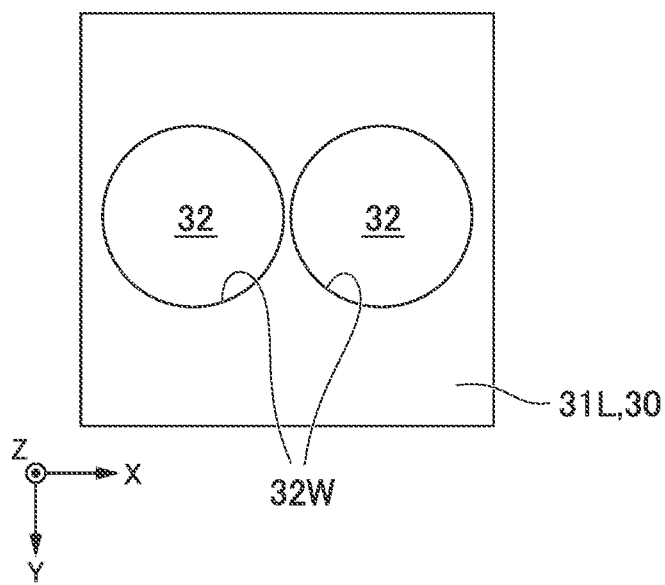
FIG. 4C is a bottom view showing a schematic configuration of the fixing member constituting the imaging module according to one or more embodiments of the invention.

FIG. 4A is a top view showing the fixing member 30 when viewed in the direction H. FIG. 4B is a side view showing the fixing member 30. FIG. 4C is a bottom view showing the fixing member 30 when viewed in the direction R. FIG. 4D is a top view showing the fixing member 30 when viewed in the direction H and is a view showing a state where the transmission harness 40 is inserted into and fixed to a through hole of the fixing member 30. Also, FIG. 4D shows a cross-sectional structure of the transmission harness 40.

The fixing member 30 has: a substrate connection face 31U (connection face, first surface) that is disposed so as to face the substrate lower face 21L of the circuit substrate 20; and a cable-drawing face 31L (second surface) opposite to the substrate connection face 31U. The fixing member 30 has two through holes 32 that penetrate through the inside of the fixing member 30. The fixing member 30 is made of an insulating member such as resin. A material used to form the fixing member 30 is not limited to a material having an insulation property, and a metal may be used.

A cross-sectional shape of the fixing member 30 is not limited to a quadrangular shape and a circular shape or an elliptical shape may be adopted. In the case of connecting the transmission harness 40 to the circuit substrate 20 by rotating the fixing member 30 at θ degrees, a cross-sectional shape of the fixing member 30 may be a circular shape. Particularly, in the case where a cross-sectional shape of the fixing member 30 is circular in shape, even where the fixing member 30 rotates at θ degrees, the fixing member 30 does not partially protrude from the external contour line of the solid-state image sensing device 10 in a plan view. Consequently, it is possible to achieve an imaging module having a small-diameter.

Furthermore, a structure may be adopted in which a projected portion is formed on the substrate connection face 31U of the fixing member 30, a recessed portion is formed on the substrate lower face 21L of the circuit substrate 20, and the projected portion and the recessed portion are fitted to each other. In this case, as the projected portion is fitted into the recessed portion, the fixing member 30 and the circuit substrate form a pair, and it is thereby possible to connect the fixing member 30 to the circuit substrate 20. In other cases, a recessed portion is formed on the substrate connection face 31U of the fixing member 30, a projected portion is formed on the substrate lower face 21L of the circuit substrate 20, and the recessed portion and the projected portion may be fitted to each other.

(Transmission Harness 40)

The transmission harness 40 is a cable into which two to four cables are collected as one body.

As shown in FIGS. 1 and 4D, the transmission harness 40 according to one or more embodiments includes the first harness 40A and the second harness 40B, and each of the first harness 40A and the second harness 40B is a coaxial cable.

The first harness 40A includes: the internal conductor 42FA (conductor) having the internal conductor end face 41FA (conductor end face); and the external conductor 42SA (conductor) having the external conductor end face 41SA (conductor end face). A coated portion 43A (insulator) is provided between the internal conductor 42FA and the external conductor 42SA, and an outer coating 44A (insulator) is provided around the periphery of the external conductor 42SA.

Similarly, the second harness 40B includes: the internal conductor 42FB (conductor) having the internal conductor end face 41FB (conductor end face); and the external conductor 42SB (conductor) having the external conductor end face 41SB (conductor end face). A coated portion 43B (insulator) is provided between the internal conductor 42FB and the external conductor 42SB, and an outer coating 44B (insulator) is provided around the periphery of the external conductor 42SB.

Each of the first harness 40A and the second harness 40B is inserted into the through hole 32 and is fixed by the fixing member 30. Specifically, the fixing member 30 has adhesive 33 that is provided between an inner wall 32W of the through hole 32 and an outer surface of the first harness 40A and between the inner wall 32W of the through hole 32 and an outer surface of the second harness 40B. After the first harness 40A and the second harness 40B are inserted into the through holes 32, the adhesive 33 is injected between the outer coating 44A and the inner wall 32W and between the outer coating 44B and the inner wall 32W, the adhesive is cured, and the first harness 40A and the second harness 40B are thereby fixed to the inside of the through holes 32.

Note that, one or more embodiments are not limited to the structure in which the first harness 40A and the second harness 40B are fixed to the inside of the through hole 32 by the adhesive 33. The first harness 40A, the second harness 40B, and the fixing member 30 may be integrally molded by resin-molding. In this case, since the through holes 32 are formed so as to correspond to outer diameters of the first harness 40A and the second harness 40B, the fixing member 30 includes an adhesion portion 34 at which the inner wall 32W of the through hole 32 is brought into close contact with each of the outer coatings 44A and 44B.

As shown in FIG. 4D, two coaxial cables are used as the transmission harness 40 in one or more embodiments; however, the transmission harness 40 is not limited to the coaxial cable, one coaxial cable and two single core cables, that is, three cables in total may be used, four single core cables may be used.

(Harness Unit 50)

The fixing member 30 and the transmission harness 40 constitute the harness unit 50.

In the harness unit 50, the fixing member 30 has not only the above-described configuration but also a connection face (substrate connection face 31U) that faces the substrate lower face 21L (circuit substrate 20) serving as a connection object. Moreover, in the harness unit 50, the internal conductor end faces 41FA and 41FB and the external conductor end faces 41SA and 41SB are exposed at the substrate connection face 31U.

Next, a method of manufacturing the harness unit 50 will be described.

A method of adhesively-fixing the transmission harness 40 to the fixing member 30 by use of adhesive (adhesive fixing method) or a method of resin-molding the transmission harness 40 (resin-molding method) is adopted.
(Adhesive Fixing Method)

In the case of fixing the first harness 40A and the second harness 40B to the fixing member 30 by use of the adhesive 33, firstly, the fixing member 30 in which the through holes 32 are formed in advance is prepared. Thereafter, the first harness 40A and the second harness 40B are each inserted into the through hole 32 and are fixed to the fixing member 30 by the adhesive 33. At this time, the internal conductor end faces 41FA and 41FB and the external conductor end faces 41SA and 41SB are each exposed inside the through hole 32 or are each exposed on the substrate connection face 31U. In this state where, by polishing or grinding the substrate connection face 31U so that the substrate connection face 31U is vertical to the transmission harness 40, the substrate connection face 31U, the internal conductor end faces 41FA and 41FB, and the external conductor end faces 41SA and 41SB are simultaneously polished or ground. As a result, the harness unit 50 is obtained in which the first harness 40A and the second harness 40B are fixed to the fixing member 30 and the internal conductor end faces 41FA and 41FB and the external conductor end faces 41SA and 41SB are exposed to the substrate connection face 31U.
(Resin-Molding Method)

In the case of fixing the first harness 40A and the second harness 40B to the fixing member 30 by integral molding, for example, a die corresponding to the shape of the fixing member 30 is prepared, and the first harness 40A and the second harness 40B are disposed inside the die. In this state, molten resin flows into the die, and the fixing member 30 is molded together with the first harness 40A and the second harness 40B. Subsequently, by polishing or grinding the substrate connection face 31U so that the substrate connection face 31U is vertical to the transmission harness 40, the substrate connection face 31U, the internal conductor end faces 41FA and 41FB, and the external conductor end faces 41SA and 41SB are simultaneously polished or ground. As a result, the harness unit 50 is obtained in which the first harness 40A and the second harness 40B are fixed to the fixing member 30 and the internal conductor end faces 41FA and 41FB and the external conductor end faces 41SA and 41SB are exposed to the substrate connection face 31U.

In the above-described harness unit 50, the positions of the conductors (internal conductor and external conductor) of the first harness 40A and the second harness 40B can be determined at a predetermined position. Moreover, by connecting the transmission harness 40 to the fixing member 30, the transmission harness 40 and the fixing member 30 which form a pair is obtained.

The internal conductor end faces 41FA and 41FB and the external conductor end faces 41SA and 41SB are located on the same plane as the substrate connection face 31U.

Note that, the internal conductor end faces 41FA and 41FB and the external conductor end faces 41SA and 41SB may protrude from the substrate connection face 31U. For example, as shown in FIG. 1, the internal conductors 42FA and 42FB and the external conductors 42SA and 42SB may include conductor protrusions 41TA and 41TB that protrude from the substrate connection face 31U, respectively. In this case, the internal conductor end faces 41FA and 41FB and the external conductor end faces 41SA and 41SB are formed on the conductor protrusions 41TA and 41TB, respectively. As a result of forming the conductor protrusions 41TA and 41TB, the internal conductor end face and the external conductor end face can be connected to the cable terminal 23 so as to the cable terminal 23, and the reliability thereof is improved.
(Electroconductive Member 60)

The electroconductive member 60 is disposed between the substrate lower face 21L of the circuit substrate 20 and the substrate connection face 31U of the fixing member 30. Since the electroconductive member 60 includes adhesive, the electroconductive member 60 connects the substrate lower face 21L to the substrate connection face 31U so that the faces are brought into close contact with each other. In other words, the substrate lower face 21L is in surface contact with the substrate connection face 31U with the electroconductive member 60 interposed therebetween. In addition, between the substrate lower face 21L and the substrate connection face 31U, the electroconductive member 60 electrically connects the internal conductor end faces 41FA and 41FB and the external conductor end faces 41SA and 41SB to the cable terminals 23FA, 23SA, 23FB, and 23SB, respectively. Specifically, as the electroconductive member 60, an anisotropic electroconductive film, anisotropic conductive paste, micro particles, or the like are adopted.
(Connection Structure)

FIG. 5 is an explanatory plan view showing the positional relationship between the electrode terminal 22 and the cable terminal 23 in the circuit substrate 20.

Figure 7:
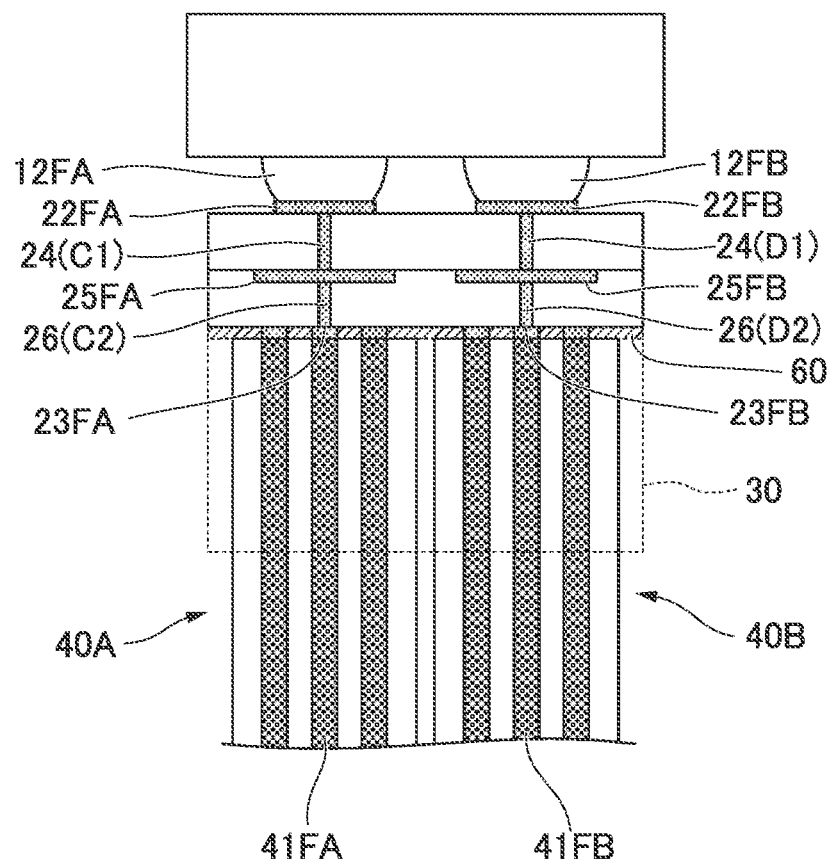
FIG. 7 is an explanatory cross-sectional view showing an electrical connection structure of the solid-state image sensing device, the circuit substrate, and the fixing member, which constitute the imaging module according to one or more embodiments of the invention.

FIGS. 6 and 7 are explanatory diagrams each showing an electrical connection structure of the solid-state image sensing device 10, the circuit substrate 20, and the fixing member 30, FIG. 6 shows a connection structure between the external conductors 42SA and 42SB and the electrode terminals 22SA and 22SB, and FIG. 7 shows a connection structure between the internal conductors 42FA and 42FB and the electrode terminals 22FA and 22FB.

As shown in FIG. 5, the positions of four electrode terminals 22FA, 22SA, 22FB, and 22SB in a plan view do not coincide with the positions of the cable terminals 23FA, 23SA, 23FB, and 23SB; however, each of the electrode terminals is electrically connected to the cable terminal via the connection wirings 24, 25, and 26.

Particularly, as shown in FIG. 6, the connection electrode 12SA is connected to the electrode terminal 22SA. The electrode terminal 22SA (second electrode terminal) is connected to the cable terminal 23SA (second cable terminal) via the connection wirings 24(A1), 25SA, and 26(A2) serving as a second connection wiring.

Similarly, the connection electrode 12SB is connected to the electrode terminal 22SB. The electrode terminal 22SB (second electrode terminal) is connected to the cable terminal 23SB (second cable terminal) via the connection wirings 24(B1), 25SB, and 26(B2) serving as a second connection wiring.

Between the substrate lower face 21L and the substrate connection face 31U, the external conductor end faces 41SA and 41SB are electrically connected to the cable terminals 23SA and 23SB, respectively, with the electroconductive member 60 interposed therebetween.

Furthermore, as shown in FIG. 7, the connection electrode 12FA is connected to the electrode terminal 22FA. The electrode terminal 22FA (first electrode terminal) is connected to the cable terminal 23FA (first cable terminal) via the connection wirings 24(C1), 25FA, and 26(C2) serving as a first connection wiring.

Similarly, the connection electrode 12FB is connected to the electrode terminal 22FB. The electrode terminal 22FB (first electrode terminal) is connected to the cable terminal 23FB (first cable terminal) via the connection wirings 24(D1), 25FB, and 26(D2) serving as a first connection wiring.

Between the substrate lower face 21L and the substrate connection face 31U, the internal conductor end faces 41FA and 41FB are electrically connected to the cable terminals 23FA and 23FB, respectively, with the electroconductive member 60 interposed therebetween.

(Method of Fixing Harness Unit 50 to Circuit Substrate 20)

Firstly, the solid-state image sensing device 10 (image-sensing device) is connected to the circuit substrate 20 so that the connection electrode 12 is electrically connected to the electrode terminal 22.

Next, the harness unit 50 is prepared. As described above, the positions of the internal conductor and the external conductor of the transmission harness 40 are determined in advance in the harness unit 50.

Subsequently, the harness unit 50 is fixed to the circuit substrate 20 with the electroconductive member 60 interposed therebetween.

Accordingly, the internal conductor end faces 41FA and 41FB and the external conductor end faces 41SA and 41SB are electrically connected to the cable terminal 23. Therefore, the circuit substrate 20 on which the solid-state image sensing device 10 is mounted is connected to the fixing member 30 to which the transmission harness 40 is fixed, and the solid-state image sensing device 10 is electrically connected to the transmission harness 40 with the circuit substrate 20 interposed therebetween.

The transmission harness 40 may be connected to the circuit substrate 20 by rotating the fixing member 30 at θ degrees so that the positions of the external conductor end face and the internal conductor end face on the cross-sectional surface of the transmission harness 40 coincide with the positions of the cable terminals of the circuit substrate 20.

According to the above-mentioned embodiment, between the substrate lower face 21L of the circuit substrate 20 and the substrate connection face 31U of the fixing member 30, it is possible to connect the conductor end faces 41FA, 41SA, 41FB, and 41SB of the transmission harness 40 to the cable terminals 23FA, 23SA, 23FB, and 23SB. Consequently, since a length required for connecting the transmission harness 40 to the circuit substrate 20 can be shorter than in a conventional case, the length of the imaging module can be shorter than in a conventional case. As a result, it is possible to provide a small imaging module. Moreover, it is possible to provide a harness unit that achieves the small imaging module.

While one or more embodiments of the invention have been described and illustrated above, it should be understood that these are exemplary of the invention and are not to be considered as limiting. Additions, omissions, substitutions, and other modifications can be made without departing from the scope of the present invention. Accordingly, the invention is not to be considered as being limited by the foregoing description, and is only limited by the scope of the appended claims.

What is claimed is:

1. An imaging module comprising:
    an image-sensing device including a connection electrode;
    a circuit substrate including:
        a substrate main body that has a first surface and a second surface opposite to the first surface, wherein the substrate main body serves as an insulating member;
        an electrode terminal that is disposed on the first surface and is electrically connected to the connection electrode;
        a cable terminal disposed on the second surface; and
        a connection wiring that is disposed inside the substrate main body and electrically connects the electrode terminal to the cable terminal;
    a fixing member having a substrate connection face disposed to face the second surface and a through hole;
    a signal cable that:
        includes a conductor having a conductor end face;
        is inserted into the through hole; and
        is fixed by the fixing member; and
    an electroconductive member that:
        is disposed between the second surface and the substrate connection face;
        connects the second surface to the substrate connection face; and
        electrically connects the conductor end face to the cable terminal at between the second surface and the substrate connection face, wherein
    the conductor of the signal cable includes an internal conductor having an internal conductor end face and an external conductor having an external conductor end face,
    the cable terminal has a first cable terminal and a second cable terminal,
    the internal conductor end face is electrically connected to the first cable terminal with the electroconductive member interposed between the second surface and the substrate connection face, and
    the external conductor end face is electrically connected to the second cable terminal with the electroconductive member interposed between the second surface and the substrate connection face.

2. The imaging module according to claim 1, wherein the conductor end face and the substrate connection face are located on a same plane.

3. The imaging module according to claim 1, wherein
    the conductor has a conductor protrusion that protrudes from the substrate connection face, and
    the conductor end face is on the conductor protrusion.

4. The imaging module according to claim 1, wherein the fixing member includes an adhesive between an inner wall of the through hole and an outer surface of the signal cable.

5. The imaging module according to claim 1, wherein the fixing member includes an adhesion portion at which an inner wall of the through hole is attached to an outer surface of the signal cable.

6. The imaging module according to claim 1, wherein
    the electrode terminal has a first electrode terminal and a second electrode,
    the connection wiring has a first connection wiring and a second connection wiring,
    the first cable terminal is electrically connected to the first electrode terminal with the first connection wiring interposed therebetween, and
    the second cable terminal is electrically connected to the second electrode terminal with the second connection wiring interposed therebetween.

7. A harness unit of the imaging module according to claim 1, the harness module comprising:
    the fixing; and
    the signal cable, wherein
    the conductor end face is exposed at the substrate connection face, and
    the substrate connection face faces a connection object.

8. The harness unit according to claim 7, wherein the conductor end face and the substrate connection face are located on a same plane.

9. The harness unit according to claim 7, wherein
the conductor has a conductor protrusion that protrudes from the substrate connection face, and
the conductor end face is on the conductor protrusion.

10. The harness unit according to claim 7, wherein the fixing member includes an adhesive between an inner wall of the through hole and an outer surface of the signal cable.

11. The harness unit according to claim 7, wherein the fixing member includes an adhesion portion at which an inner wall of the through hole is attached to an outer surface of the signal cable.

* * * * *